(12) United States Patent
Jonsson et al.

(10) Patent No.: US 11,065,157 B2
(45) Date of Patent: Jul. 20, 2021

(54) TAMPON APPLICATOR

(71) Applicant: Essity Hygiene and Health Aktiebolag, Gothenburg (SE)

(72) Inventors: Sylvia Jonsson, Gothenburg (SE); Conny Dahlqvist, Gothenburg (SE); Susanne Carlstedt, Malmö (SE); Malkus Arlemark, Malmö (SE)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 0 days.

(21) Appl. No.: 16/649,245

(22) PCT Filed: Oct. 6, 2017

(86) PCT No.: PCT/EP2017/075539
§ 371 (c)(1),
(2) Date: Mar. 20, 2020

(87) PCT Pub. No.: WO2019/068348
PCT Pub. Date: Apr. 11, 2019

(65) Prior Publication Data
US 2020/0237574 A1  Jul. 30, 2020

(51) Int. Cl.
*A61F 13/26* (2006.01)
(52) U.S. Cl.
CPC .................. *A61F 13/266* (2013.01)
(58) Field of Classification Search
CPC .......... A61F 13/26; A61F 13/266; A61F 6/12; A61F 6/18
See application file for complete search history.

(56) References Cited

U.S. PATENT DOCUMENTS

| | | | |
|---|---|---|---|
| 3,645,263 A | 2/1972 | Bates | |
| 3,765,416 A | 10/1973 | Werner et al. | |
| 3,835,856 A | 9/1974 | Warncke | |
| 4,361,150 A | 11/1982 | Voss | |
| 4,479,791 A | 10/1984 | Sprague | |
| 4,676,773 A | 6/1987 | Sheldon | |
| 4,891,042 A | 1/1990 | Melvin et al. | |
| 4,960,417 A | 10/1990 | Tarr et al. | |
| 5,080,659 A * | 1/1992 | Nakanishi | A61F 13/263 604/15 |

(Continued)

FOREIGN PATENT DOCUMENTS

| CA | 945703 A | 4/1974 |
|---|---|---|
| CN | 1229351 A | 9/1999 |

(Continued)

OTHER PUBLICATIONS

International Preliminary Report on Patentability for International Application No. PCT/EP2017/075539, dated Sep. 16, 2019. 12 pages.

(Continued)

*Primary Examiner* — Tatyana Zalukaeva
*Assistant Examiner* — Heather K Barnwell
(74) *Attorney, Agent, or Firm* — Wood Herron & Evans LLP

(57) ABSTRACT

An applicator for a tampon is provided. The applicator has an inner tube and an outer tube. The inner tube is slideable within the outer tube. The applicator has a forward end and a rear end, and the inner tube has at least one inwardly protruding flange.

17 Claims, 4 Drawing Sheets

(56) References Cited

U.S. PATENT DOCUMENTS

| | | |
|---|---|---|
| 5,554,109 A | 9/1996 | Frayman |
| 5,569,177 A | 10/1996 | Fox et al. |
| 5,571,540 A | 11/1996 | Weyenberg et al. |
| 6,019,744 A | 2/2000 | Altdorf et al. |
| 2003/0028138 A1 | 2/2003 | Karapasha et al. |
| 2003/0144639 A1* | 7/2003 | Gehling ............... A61F 13/8405 604/360 |
| 2005/0273043 A1* | 12/2005 | Osborn, III ............ A61F 13/26 604/15 |
| 2008/0154176 A1 | 6/2008 | Van Ingelgem et al. |
| 2008/0195029 A1* | 8/2008 | Van Ingelem ...... A61F 13/2034 604/14 |
| 2009/0192436 A1 | 7/2009 | Karapasha et al. |
| 2010/0016780 A1 | 1/2010 | VanDenBogart et al. |
| 2010/0324468 A1 | 12/2010 | Gann et al. |
| 2011/0201992 A1 | 8/2011 | Smet et al. |
| 2011/0273727 A1* | 11/2011 | Seki ...................... A61F 13/266 356/634 |
| 2016/0296380 A1 | 10/2016 | Graham et al. |

FOREIGN PATENT DOCUMENTS

| | | |
|---|---|---|
| CN | 101155568 A | 4/2008 |
| CN | 101346114 A | 1/2009 |
| CN | 102088942 A | 6/2011 |
| CN | 102341080 A | 2/2012 |
| CN | 103384508 A | 11/2013 |
| CN | 206007475 U | 3/2017 |
| EP | 1695680 A1 | 8/2006 |
| EP | 1704841 A1 | 9/2006 |
| EP | 2404585 A1 | 1/2012 |
| GB | 2220359 A | 1/1990 |
| RU | 2406473 C2 | 12/2010 |
| WO | 9011747 A1 | 10/1990 |
| WO | 9711747 A1 | 4/1997 |
| WO | 2007115091 A1 | 10/2007 |
| WO | 2010046478 A1 | 4/2010 |
| WO | 2016156403 A1 | 10/2016 |

OTHER PUBLICATIONS

International Search Report and Written Opinion for International Application PCTEP2017/075539, dated Jan. 25, 2018, 11 pages.
International Search Report and Written Opinion for International Application No. PCT/EP2017/075541, dated Feb. 12, 2018, 8 pages.
International Preliminary Report on Patentability for International Application No. PCT/EP2017/075542, dated Aug. 9, 2019, 11 pages.
International Search Report and Written Opinion for International Application PCT/EP2017/075542, dated Feb. 14, 2018, 9 pages.
International Preliminary Report on Patentability for International Application No. PCT/EP2017/075543, dated Sep. 18, 2019, 13 pages.
International Search Report and Written Opinion for International Application PCT/EP2017/075543, dated Feb. 14, 2018, 8 pages
Federal Service for Intellectual Property, Decision to Grant, Russian Application No. 2020115156, dated Aug. 27, 2020 (17 pages).
Federal Service for Intellectual Property, Decision to Grant, Russian Application No. 2020115119, dated Aug. 14, 2020 (18 pages).
Federal Service for Intellectual Property, Decision to Grant, Russian Application No. 2020115036, dated Aug. 14, 2020 (18 pages).
China National Intellectual Property Administration, Office Action, Application No. 201780094581.1, dated Aug. 10, 2020 (8 pages).
China National Intellectual Property Administration, Office Action, Application No. 201780094573.7 dated Aug. 7, 2020 (10 pages).
China National Intellectual Property Administration, Office Action, Application No. 201780094572.2 dated Aug. 7, 2020 (11 pages).
China National Intellectual Property Administration, Second Office Action, Application No. 201780094581.1, dated Apr. 8, 2021 (22 pages).

* cited by examiner

TAMPON APPLICATOR

CROSS REFERENCE TO RELATED APPLICATIONS

This is a U.S. National Phase application of PCT/EP2017/075539, filed Oct. 6, 2017, the disclosure of which is incorporated herein by reference in its entirety for all purposes.

TECHNICAL FIELD

The present disclosure relates to tampon applicators.

BACKGROUND

Tampons are female hygiene absorbent products used to absorb menstrual blood flow within the body of a user. Tampons may be provided with or without applicators. When no applicator is provided, the tampon is generally inserted manually by the user. However many women prefer to use an applicator to facilitate insertion of the tampon and/or for hygiene reasons.

Known tampon applicators generally include two cylindrical tubes arranged in a telescopic relationship with each other, one tube being slideable within the other tube. In one arrangement, the tampon is provided within the outer tube whilst the inner tube is provided within the outer tube behind the tampon and extending outside of the outer tube in a rearward direction. In use, the user inserts the outer tube into the body and pushes the rearwardly extending portion of the inner tube in a forward direction towards the tampon, and the front part of the inner tube makes contact with and pushes the tampon out of the outer tube and into the body of the user. It will be appreciated that, as the inner tube is only partially inserted into the outer tube, such applicators are relatively bulky.

In another arrangement, where the applicators may be referred to as "compact" or "collapsible" applicators, the tampon is located in the inner tube and the inner tube is almost entirely contained within the outer tube. This provides a more compact and discreet applicator. In such applicators, the tampon generally has a mushroom-cap shaped front end which protrudes from the front part of the inner tube and which prevents the tampon from being entirely contained within the inner tube. In use, the user first pulls an exposed rear part of the inner tube in a rearward direction so that the inner tube slides rearwardly with respect to the outer tube, thereby exposing most of the inner tube. A forward part of the inside surface of the outer tube may include protrusions which protrude inwardly and which contact the mushroom-cap shaped front end of the tampon to help to hold the tampon in place whilst the inner tube is being rearwardly extended. In this manner, the tampon stays in position with respect to the outer tube whilst the inner tube slides backwards and extends rearwardly of the outer tube. This movement of the inner tube relative to the tampon and the outer tube results in the inner tube sliding in a rearward direction over the tampon and leaving the tampon within the outer tube. Once the tampon is no longer held within the inner tube and the inner tube is positioned rearwardly of the tampon, the outer tube may be inserted into the body of the user and the rearwardly extending portion of the inner tube may be pushed in a forward direction towards the tampon. As explained previously, the front part of the inner tube will then make contact with the tampon and push the tampon out of the outer tube and into the body of the user.

Tampons usually include a string extending from the rear end of the tampon to facilitate removal of the tampon from the body of the user. It has been observed that it is very common for users to check that the string is firmly attached to the tampon before they insert the tampon. In the first arrangement described above, the inner tube is positioned behind the tampon and prevents the user from pulling the tampon out of the outer tube when the string is pulled. However, in the more compact arrangement, the user generally pulls the string to test its security when the tampon is located in the inner tube. In this case, the mushroom-cap shaped forward end part of the tampon engages with the front of the inner tube and prevents the tampon from sliding backwards through the inner tube and out of the applicator.

However, although the mushroom-cap shaped forward end part of the tampon is practical in this regard, many users have complained that this makes the tampon uncomfortable and difficult to insert. As a response, many newer tampons now do not have a mushroom-cap shaped forward end part and may instead have a more streamlined forward end part to aid insertion into the body. However, when the users check the security of the string of such tampons, it is not uncommon for the tampon to be pulled backwards through the inner tube and out of the applicator. Once the tampon is outside of the applicator it is very difficult to replace.

It would be desirable to provide an applicator that is of the compact type and which is able to be used with more streamlined tampons (such as ones without a mushroom-cap shaped forward end) whilst maintaining the tampon in the inner tube even if the user checks the string vigorously.

SUMMARY

According to the present disclosure there is provided an applicator for a tampon comprising an inner tube and an outer tube, the inner tube being slideable within the outer tube, the applicator having a forward end and a rear end, wherein the inner tube comprises at least one inwardly protruding flange.

The applicator may be of a compact type. The inner tube of the applicator may be configured to receive a tampon. The forward end refers to the front or distal end of the applicator, ie the part of the applicator which is inserted into the body. The rear or rearward end refers to the back or proximal end of the applicator, ie the part of the applicator which is not inserted into the body and which is handled by the user.

The flange may extend inwardly and towards the forward end of the applicator. The flange may extend from an inner surface of the inner tube inwardly towards the forward end of the applicator.

The acute angle between the flange and the inner surface of the inner tube may be in the range of 5 degrees to 85 degrees. The acute angle between the flange and the inner surface of the inner tube may be in the range of 10 degrees to 45 degrees.

The flange may be formed integrally with the inner tube. The flange may be formed by a notch in the inner tube.

The flange may be substantially a "U" shaped flange. The "U" shaped flange may have two sides extending from the inner tube and a further side extending between said two sides and forming the bottom of the "U" shape, the two sides of the "U" shaped flange being the same or shorter in length than the length of the further side forming the bottom of the "U" shape.

A plurality of inwardly protruding flanges may be provided on the inner tube. Said plurality of flanges may be equally spaced around the circumference of the inner tube. Each of the flanges may be located at the same longitudinal position with respect to the longitudinal length of the inner tube. The flanges may be positioned around the circumference of the inner tube at that same longitudinal position. The flanges may be equally spaced around the circumference of the inner tube at that same longitudinal position.

Alternatively, at least two of the flanges may be located at different longitudinal positions from each other with respect to the longitudinal length of the inner tube.

The flange or flanges may be located at between 10% and 90% of the longitudinal length of the inner tube. The flange or flanges may be located at between 30% and 70% of the longitudinal length of the inner tube. The flange or flanges may be located approximately mid-way between the rear end and the forward end of the inner tube.

The inner tube and the outer tube may be formed from a thermoplastic material, such as a medical device classified thermoplastic material for example. The inner and outer tube may be formed from low density polyethylene (LDPE). The inner tube may be formed from a more rigid material or a stiffer material than the outer tube. For example, the outer tube may be formed from LDPE and the inner tube may be formed from polypropylene (PP). This permits the outer tube to be formed from a softer and/or more resilient material than the inner tube so that the outer tube is more comfortable when inserted into the body of a user. The inner tube may be formed of a more rigid or stiffer material to assist in pushing the tampon out from the outer tube of the applicator into the body of a user.

The applicator may further include a tampon disposed in the inner tube. At least one flange may be configured to engage the tampon. A plurality of flanges may be configured to engage the tampon. The applicator may consist of or comprise an inner tube and an outer tube. The applicator may consist of or comprise an inner tube and an outer tube and a tampon disposed in the inner tube.

BRIEF DESCRIPTION OF THE DRAWINGS

The present invention will now be described by way of example only and with reference to the following drawings, of which.

DETAILED DESCRIPTION OF PARTICULAR EMBODIMENTS

Figure 1:
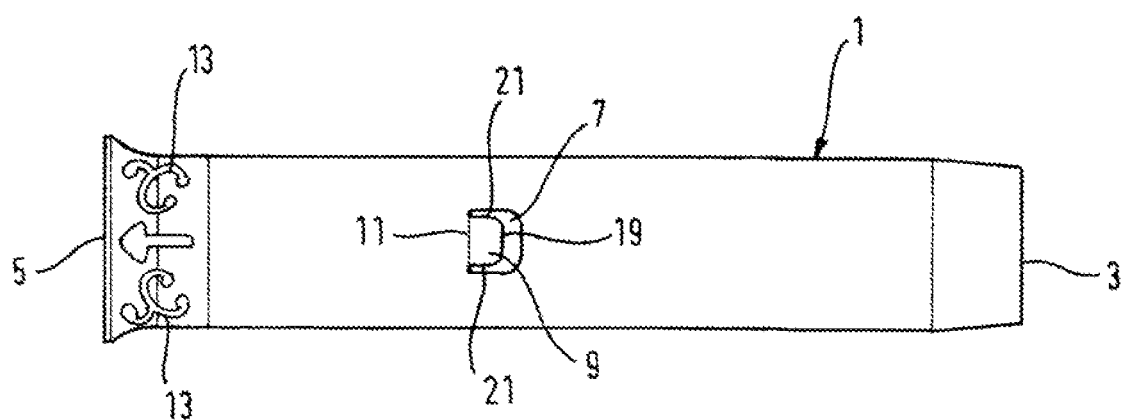
FIG. 1 is a plan view of an inner tube of a tampon applicator in accordance with an embodiment of the invention.

An inner tube 1 of a tampon applicator is shown in FIG. 1. The inner tube 1 has a front end 3 and a rear end 5. In this embodiment, the inner tube 1 has a "U" shaped notch 7 formed therein which defines a "U" shaped flange or tab 9 having two sides 21 and a bottom 19. In this embodiment, the flange 9 is formed integrally with the inner tube, however in other embodiments the flange 9 may be a separate part which is attached to the inner tube and which protrudes into the interior space within the inner tube. In such embodiments the flange 9 may be attached to an inner surface 15 of the inner tube 1 and a notch 7 may not be required.

The flange 9 is bent inwardly about a bend line 11 such that the flange 9 protrudes into the interior space within the inner tube.

The front end 3 of the inner tube may be tapered such that the inner tube is narrower at the front end 3 than at the rear end 5. A tapered inner tube front end 3 may assist in engaging with the rear end of a tampon and in pushing the tampon out of an outer tube of an applicator.

The rear end 5 of the inner tube 1 may be tapered such that the rear end 5 of the inner tube 1 is wider than the remainder of the inner tube 1. This may assist in preventing the inner tube from being pushed entirely within an outer tube. The rear end 5 of the inner tube may include decorative or grip features 13 which may assist a user to firmly grip the rear end 5 of the inner tube 1 between their fingers, thereby facilitating use of the applicator.

Figure 2:
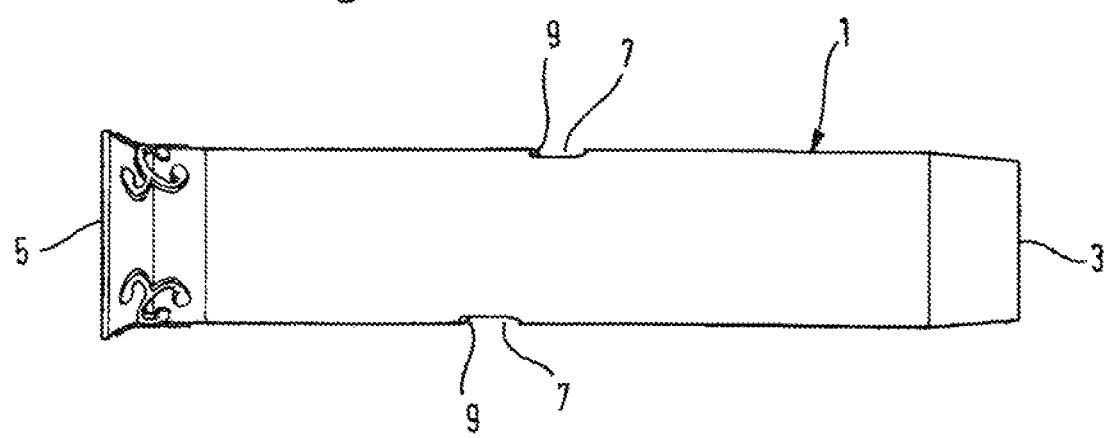
FIG. 2 is a side view of the inner tube of FIG. 1.

FIG. 2 shows the inner tube 1 of FIG. 1 having been rotated around its longitudinal axis by approximately 90 degrees. It can be seen that, in this embodiment, there are two notches 7 provided in the inner tube 1 and two corresponding flanges or tabs 9. The flanges 9 protrude into the interior space within the inner tube 1. Although this embodiment shows two flanges, in other embodiments only one flange, or alternatively more than two flanges, may be provided. Where two or more flanges are provided, the flanges may be positioned approximately equidistantly from each other around the circumference of the inner tube, or alternatively the flanges may not be positioned equidistantly from each other around the circumference of the inner tube.

The embodiment shown in FIG. 2 provides that the flanges 9 are not located at the same longitudinal position along the longitudinal axis of the inner tube but are instead offset such that they are located at different longitudinal positions along the longitudinal axis of the inner tube.

Figure 4:
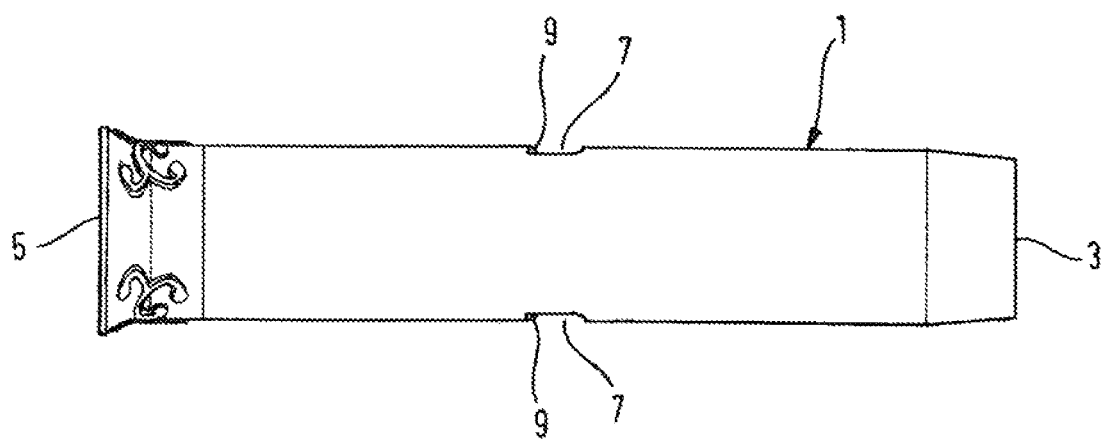
FIG. 4 is a side view of an inner tube of a tampon applicator in accordance with a further embodiment of the invention.

An alternative embodiment is shown in FIG. 4, where the flanges 9 are located at approximately the same longitudinal position along the longitudinal axis X of the inner tube.

Figure 3:
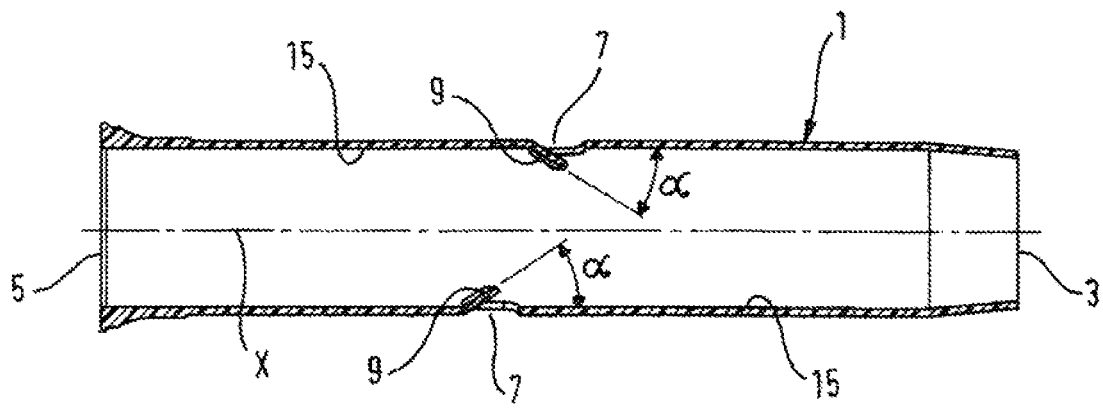
FIG. 3 shows a longitudinal cross-section of the inner tube of FIG. 2.

FIG. 3 shows a longitudinal cross-section through the inner tube of FIGS. 1 and 2. From FIG. 3 it can be seen that the flanges 9 protrude inwardly into the interior space defined by the inner tube 1. According to certain embodiments, the angle α between the inner surface 15 of the inner tube and the flange 9 is preferably less than 90 degrees. This permits a tampon located within the inner tube to move in a forward direction without undue interference from the flange 9, but the flange 9 hinders movement of the tampon in a rearward direction. The angle α may be in the range of 5 degrees to 85 degrees or in the range of 10 degrees to 45 degrees. In this particular embodiment, the angle α is approximately 20 degrees. This permits the flange 9 to protrude sufficiently into the interior space defined by the inner tube in order to prevent rearward movement of the tampon, and without undue stress being placed on the flange 9 so that it is less likely to fracture at the bend line 11. Furthermore, such an arrangement still permits easy forward movement of the tampon.

As can be seen from FIG. 1, the flange 9 of this embodiment has two sides 21 and a bottom 19, the sides 21 being of a shorter length than the bottom 19. This arrangement may prevent the flange from breaking during use, as it is likely to be more stable than a "U" shaped flange having a bottom 19 of a shorter length than the sides 21. However, in other embodiments of the invention the bottom 19 may be the same length or a shorter length than the sides 21.

Figure 5:
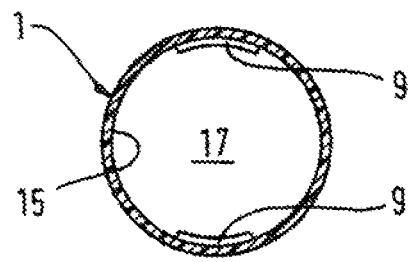
FIG. 5 is an end view of the inner tube of FIG. 1.

FIG. 5 shows an end view of the inner tube of FIG. 1. The flanges 9 can be seen protruding into the interior space 17 defined by the inner tube 1.

Figure 6:
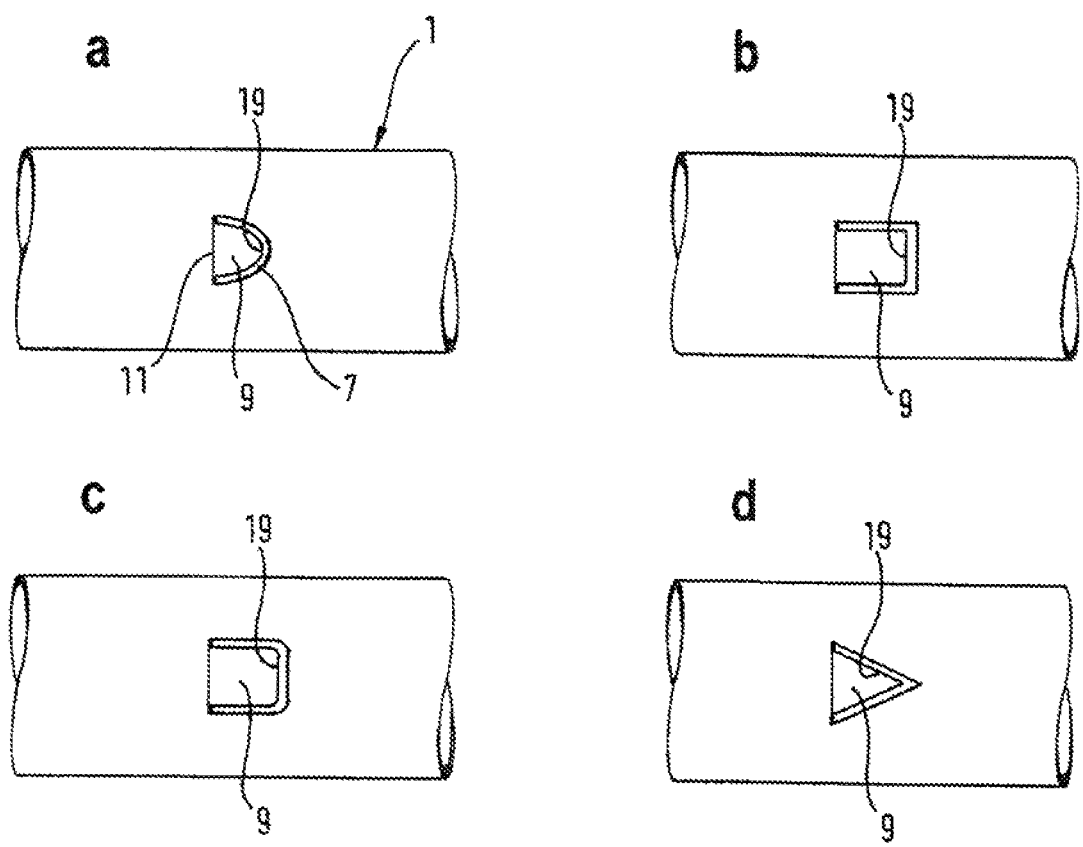
FIGS. 6a to 6d show partial plan views of inner tubes in accordance with further embodiments of the invention.

The flange 9 of the previous embodiments is a "U" shaped flange, however in other embodiments of the invention the flange(s) 9 may have other shapes, as shown in FIGS. 6a to 6d. "U" shaped flanges having a round bottom 19 such as shown in FIG. 6a are contemplated, as are "U" shaped flanges having a flat bottom 19 as shown in FIG. 6c. "U" shaped flanges being of a square or rectangular shape as shown in FIG. 6b are also contemplated. In other embodiments of the invention, the flange may be of a "V" shape such as that shown in FIG. 6d, or may indeed be of any other suitable shape. "U" shaped flanges may be advantageous in that they do not have a point at their bottom 19 which might cause the flange 9 to become engaged with the tampon and thereby hinder the forward movement of the tampon during insertion into the body of the user. As explained above, it may be advantageous to provide "U" shaped flanges having sides 21 which are of a shorter length than the bottom 19 of the flange 9.

Figure 7:
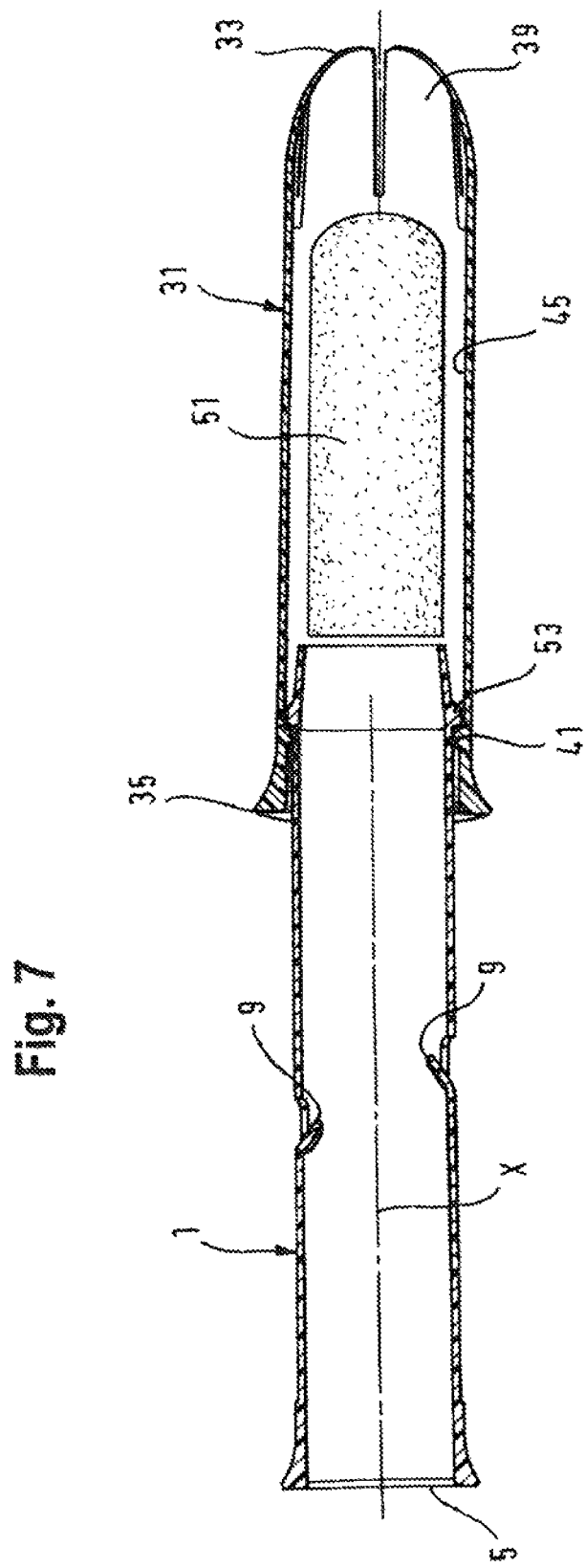
FIG. 7 shows a longitudinal cross-sectional view through a tampon applicator in accordance with an embodiment of the invention.

FIG. 7 shows a tampon applicator including an outer tube 31 and an inner tube 1. The outer tube 31 has a forward end 33 and a rear end 35. In this embodiment, the outer tube 31 includes a plurality of petals 39 at its forward end 33. In this embodiment, towards the rear end 35 of the outer tube 31 there is an annular protrusion 41 which extends circumferentially around the interior surface 45 of the outer tube 31 and which protrudes radially inwards into the interior space defined by the outer tube 31. In this embodiment, the inner tube 1 has a radially outwardly protruding rim 53 near the forward end of the inner tube 1 for engaging with the annular protrusion 41 of the outer tube 31 to prevent the inner tube from sliding backwards completely out of the outer tube during use of the applicator.

As can be seen in FIG. 7, the internal diameter of the outer tube is slightly greater than the external diameter of the inner tube, to enable the inner tube to slide within the outer tube. Initially, a tampon 51 is at least partly located within the inner tube and the inner tube is almost entirely located within the outer tube, except for the rearmost part of the inner tube. To use the applicator, a user grips the rearmost part of the inner tube and slides the inner tube backwards relative to the outer tube. Means, such as spikes, may be provided on the interior forward end of the outer tube in order to hold the tampon in position relative to the outer tube whilst the inner tube slides relative to the outer tube. This allows the inner tube to slide rearwardly away from the tampon and to leave the tampon in the outer tube 31. The inner tube 1 is then positioned behind the tampon 51 as shown in FIG. 7. The tampon 51 is now ready to be inserted into the body of the user, by pushing the inner tube 1 in a forwards direction back into the outer tube 31.

It will be seen that the present invention provides a means for restricting rearwards movement of the tampon in the inner tube whilst still permitting unrestricted forwards movement of the tampon, and without restricting the slideability of the inner tube relative to the outer tube of the applicator. By restricting the rearwards movement of the tampon in the inner tube, if the string is pulled to check it is securely attached to the tampon whilst the tampon is in the inner tube, the tampon will be prevented from sliding rearwardly out of the inner tube.

While the foregoing description and drawings represent exemplary embodiments of the present invention, it will be understood that various additions, modifications and substitutions may be made therein without departing from the spirit and scope of the present invention. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

The invention claimed is:

1. An applicator for a tampon, comprising:
an inner tube and an outer tube, the inner tube being slideable within the outer tube, the applicator having a forward end and a rear end, wherein the inner tube comprises a tampon at least partially disposed in the inner tube, a front end configured to engage with a rear end of the tampon, with the inner tube being located entirely rearwardly of the tampon when the tampon is being pushed out of the outer tube of the applicator during movement of the inner tube relative to the outer tube in a direction toward the forward end of the applicator, and at least one flange disposed on the inner tube and protruding into an interior space within the inner tube and being configured to engage the tampon when it is at least partially disposed in the inner tube, wherein the at least one flange is located at between 10% and 90% of the longitudinal length of the inner tube.

2. The applicator for a tampon according to claim 1, wherein the at least one flange extends inwardly and towards the forward end of the applicator.

3. The applicator for a tampon according to claim 1, wherein the at least one flange extends from an inner surface of the inner tube inwardly towards the forward end of the applicator.

4. The applicator for a tampon according to claim 1, wherein an acute angle between the at least one flange and the inner surface of the inner tube is in a range of 5 degrees to 85.

5. The applicator for a tampon according to claim 1, wherein the inner tube and the flange are formed by a moulding process.

6. The applicator for a tampon according to claim 1, wherein the at least one flange is formed integrally with the inner tube.

7. The applicator for a tampon according to claim 1, wherein the at least one flange is substantially a "U" shaped flange.

8. The applicator for a tampon according to claim 7, wherein the "U" shaped flange has two sides extending from the inner tube and a further side extending between said two sides and forming the bottom of the "U" shape, the two sides of the "U" shaped flange being the same or shorter in length than a length of the further side forming the bottom of the "U" shape.

9. The applicator for a tampon according to claim 1, wherein a plurality of inwardly protruding flanges are provided on the inner tube.

10. The applicator for a tampon according to claim 9, wherein the plurality of flanges are equally spaced around a circumference of the inner tube.

11. The applicator for a tampon according to claim 9, wherein each of the plurality of flanges is located at the same longitudinal position with respect to the longitudinal length of the inner tube, the plurality of flanges being positioned around the circumference of the inner tube at that longitudinal position.

12. The applicator for a tampon according to claim 9, wherein at least two of the plurality of flanges are located at different longitudinal positions from each other with respect to the longitudinal length of the inner tube.

13. The applicator for a tampon according to claim 1, wherein the at least one flange is located at between 30% and 70% of the longitudinal length of the inner tube.

14. An applicator for a tampon according to claim 1, wherein the at least one flange is located approximately mid-way between the rear end and the forward end of the inner tube.

15. An applicator for a tampon according to claim 1, wherein the inner tube is formed from a stiffer material than the outer tube.

16. The applicator for a tampon according to claim 1, wherein an acute angle between the at least one flange and the inner surface of the inner tube is in a range of 10 degrees to 45 degrees.

17. The applicator for a tampon according to claim 1, wherein the at least one flange is formed by a notch in the inner tube.

* * * * *

UNITED STATES PATENT AND TRADEMARK OFFICE
CERTIFICATE OF CORRECTION

PATENT NO. : 11,065,157 B2
APPLICATION NO. : 16/649245
DATED : July 20, 2021
INVENTOR(S) : Sylvia Jonsson et al.

Page 1 of 1

It is certified that error appears in the above-identified patent and that said Letters Patent is hereby corrected as shown below:

In the Claims

In Claim 4, Column 6, Line 54, change "to 85." to --to 85 degrees.--.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*